US 8,535,284 B2

(12) United States Patent
Ramella et al.

(10) Patent No.: US 8,535,284 B2
(45) Date of Patent: *Sep. 17, 2013

(54) DRAINAGE PUMP UNIT

(75) Inventors: Ivo Ramella, Ebikon (CH); Fabian Joder, Baar (CH)

(73) Assignee: Medela Holding AG, Baar (CH)

(*) Notice: Subject to any disclaimer, the term of this patent is extended or adjusted under 35 U.S.C. 154(b) by 429 days.

This patent is subject to a terminal disclaimer.

(21) Appl. No.: 12/300,983

(22) PCT Filed: May 16, 2008

(86) PCT No.: PCT/CH2008/000225
§ 371 (c)(1),
(2), (4) Date: Mar. 18, 2010

(87) PCT Pub. No.: WO2008/141471
PCT Pub. Date: Nov. 27, 2008

(65) Prior Publication Data
US 2010/0174227 A1    Jul. 8, 2010

(30) Foreign Application Priority Data
May 22, 2007 (CH) .......................................... 823/07

(51) Int. Cl.
*A61F 5/44* (2006.01)
(52) U.S. Cl.
USPC .......................................... 604/335; 604/317
(58) Field of Classification Search
USPC .............. 604/355, 319, 313–324, 257–260, 604/540–543, 335, 19; 4/144.3; 128/912; 417/4
See application file for complete search history.

(56) References Cited

U.S. PATENT DOCUMENTS

| 3,957,052 A | 5/1976 | Topham |
| 4,883,476 A | 11/1989 | Kurtz et al. |

(Continued)

FOREIGN PATENT DOCUMENTS

| DE | 29911438 | 12/2000 |
| EP | 1184043 | 3/2002 |

(Continued)

OTHER PUBLICATIONS

English translation of the International Preliminary Report on Patentability for corresponding International App. No. PCT/CH2008/000225.

(Continued)

*Primary Examiner* — Jacqueline Stephens
*Assistant Examiner* — Benedict L Hanrahan
(74) *Attorney, Agent, or Firm* — McDonnell Boehnen Hulbert & Berghoff LLP

(57) ABSTRACT

The drainage pump unit according to the invention for aspirating body fluids by means of a suction pump comprises a drainage pump device with a pump housing (4) for receiving the suction pump, and a fluid collection container (5) that can be secured releasably on the pump housing (4). The drainage pump unit also comprises a pump-side attachment part (2) which has a connection element for connection to a patient-side drainage tube (10). The attachment part (2) is held releasably on the pump housing (4), and it has a connector piece (20) onto which an attachment opening (54) of the fluid collection container (5) can be fitted. Alternatively, the attachment part (2) can have an attachment opening into which a connector piece of the fluid collection container (5) can be inserted. The connection element and the connector piece (20) or attachment opening are connected to each other via a drainage channel (24) extending through the attachment part (2). This drainage pump unit allows the fluid collection container to be replaced without removing the drainage tube and, therefore, without disturbing the patient.

13 Claims, 6 Drawing Sheets

(56) References Cited

U.S. PATENT DOCUMENTS

| | | | |
|---|---|---|---|
| 5,466,229 A * | 11/1995 | Elson et al. | 604/317 |
| 5,507,734 A | 4/1996 | Everett, Jr. et al. | |
| 6,352,525 B1 | 3/2002 | Wakabayashi | |
| 6,358,218 B1 | 3/2002 | Want et al. | |
| 6,394,996 B1 | 5/2002 | Lawrence et al. | |
| 6,755,807 B2 | 6/2004 | Risk, Jr. et al. | |
| 2001/0031943 A1 | 10/2001 | Urie | |
| 2002/0058915 A1 | 5/2002 | Wakabayashi | |
| 2002/0161317 A1 | 10/2002 | Risk et al. | |
| 2003/0163101 A1 | 8/2003 | Say | |
| 2004/0024360 A1 | 2/2004 | Greter et al. | |
| 2004/0208756 A1 | 10/2004 | Adahan | |
| 2005/0171495 A1 | 8/2005 | Austin et al. | |
| 2006/0036221 A1 | 2/2006 | Watson | |

FOREIGN PATENT DOCUMENTS

| | | |
|---|---|---|
| EP | 1219311 | 7/2002 |
| GB | 2307180 | 5/1997 |
| GB | 2378734 | 2/2003 |
| JP | 2001-507971 | 6/2001 |
| WO | 96/05873 | 2/1996 |
| WO | 98/30270 | 7/1998 |
| WO | 03/016719 | 2/2003 |
| WO | 2005/061025 | 7/2005 |
| WO | 2007/128156 A2 | 11/2007 |

OTHER PUBLICATIONS

International Search Report from European Application 09012685 mailed Dec. 11, 2009.

International Preliminary Report on Patentability for PCT/CH2007/000220 mailed on Dec. 10, 2008, issued Dec. 10, 2008.

English translation of the Int. Search Report and Written Opinion for International App. No. PCT/CH2007/000220, dated Dec. 4, 2008.

English translation of the Int. Search Report and Written Opinion for International App. No. PCT/CH2008/000225, completed Sep. 3, 2008.

* cited by examiner

DRAINAGE PUMP UNIT

CROSS-REFERENCE TO RELATED APPLICATIONS

The present application is a U.S. National Phase Application pursuant to 35 U.S.C. §371 of International Application No. PCT/CH2008/000225 filed on May 16, 2008, which claims priority to Swiss application No. 00823/07 filed on May 22, 2007. The entire contents of each of these applications are incorporated by reference herein.

TECHNICAL FIELD

The invention relates to a drainage pump unit according to the preamble of Patent Claim 1.

PRIOR ART

Drainage pump systems are used to aspirate body liquids and fluids in the medical field, for example during or after surgical interventions, but also in wound drainage, thorax drainage or liposuction. These drainage pump systems usually have a suction pump, one or more fluid collection containers and a drainage tube connection between patient and fluid collection container. The fluid collection container can be secured releasable on the housing of the drainage pump or can be connected to the pump via a vacuum tube.

With an underpressure being generated in the fluid collection container by means of the suction pump or vacuum pump, the fluid or secretion from a cavity in the patient is aspirated through the drainage tube and into the collection container and is collected therein. Filters arranged on the pump-side outlet of the collection container protect the suction pump from contamination by the aspirated fluid. A fluid collection container of this kind with a rigid cover and with a flexible bag secured thereon is known, for example, from EP 0 861 668 and WO 01/24846.

EP 0 466 334 discloses a drainage line with a drainage catheter and an airtight sleeve surrounding the catheter. At both of its ends, the catheter is connected to an attachment part. A connector for a gas analyzer is provided on the patient-side attachment part.

In addition to the drainage line, it is also known to run a service line from the pump to the patient. For example, U.S. Pat. No. 5,738,656 uses a double-lumen tube, one lumen forming the drainage line, and the second lumen being an air conduit which, at the patient-side end, opens into the drainage line. In this way, air or gas can be fed into the patient cavity to be aspirated, and the cavity can thus be flushed. This lumen can additionally be used as a measurement line for determining flow differences or pressure differences. In this way, the drainage procedure can be optimally monitored and also automatically controlled.

In WO 05/061025, a service line connected to the patient-side end of the drainage tube is used to flush the drainage line, in order to avoid or to eliminate occlusion of the line by aspirated clots or tissues.

U.S. Pat. No. 6,626,827 describes a drainage tube unit with two tubes, which drainage tube unit has a y-shaped attachment part at the pump-side end. At the patient-side end, the two tubes open into two independent attachment parts.

U.S. Pat. No. 5,029,580 discloses a drainage tube unit with a double-lumen tube, which contains a drainage line and an air delivery line. At the patient-side end, the tube has internal through-openings that connect the two lines to each other. At its ends, this tube is provided with a pump-side attachment part and a patient-side attachment part. Further connection possibilities are also provided in these attachment parts.

U.S. Pat. No. 5,134,996 discloses a multi-lumen drainage tube which is surrounded by a sleeve and which, at its two ends, is provided with attachment parts.

Although these connectors, by virtue of their attachment parts, avoid incorrect manipulations, they nevertheless have a relatively complicated structure, particularly since they are composed of a plurality of individual parts. In addition, they can also only be used with a double-lumen catheter tube, in particular only with a tube that has a specially designed patient-side end. However, since these drainage tube units cannot be used more than once and are discarded as disposable parts after one use, they have to be as inexpensive as possible.

A disadvantage of the systems according to the prior art is, furthermore, that the drainage tubes always have to be removed from the fluid collection container when the latter is emptied. This causes unnecessary disturbance of the patient.

DISCLOSURE OF THE INVENTION

It is therefore an object of the invention to make available a drainage pump unit that reduces disturbance of the patient to a minimum.

This object is achieved by a drainage pump unit with the features of Patent Claim 1.

The drainage pump unit according to the invention for aspirating body fluids by means of a suction pump comprises a drainage pump device with a pump housing for receiving the suction pump, and a fluid collection container that can be secured releasably on the pump housing. The drainage pump unit also comprises a pump-side attachment part which has a connection element for connection to a patient-side drainage tube. The attachment part is held releasably on the pump housing and it has a connector piece onto which an attachment opening of the fluid collection container can be fitted. Alternatively, the attachment part can have an attachment opening into which a connector piece of the fluid collection container can be inserted. The connection element and the connector piece or attachment opening are connected to each other via a drainage channel extending through the attachment part.

Since the drainage tube or the attachment part is not now held in the fluid collection container, but instead in or on the pump housing, and can be connected to the fluid collection container, the fluid collection container can be removed and emptied or replaced, without the drainage tube having to be removed. It can remain inserted in the pump housing. The patient is therefore not inconvenienced, since the drainage tube does not have to be touched or moved.

The connection between pump-side attachment part and fluid collection container is preferably made directly, i.e. without intermediate tubes or intermediate conduits.

The pump housing preferably has a recess in which the attachment part is held releasably and, in particular, into which it can be plugged. In this way, the attachment part is held securely and is also not moved upon release of the fluid collection container.

In a preferred embodiment, the recess is located in a wall of the pump housing directed towards the fluid collection container. The recess preferably extends as far as an edge of the wall and thus forms a corner piece. It is advantageous if the edge is an upper edge.

The attachment part is preferably held in a form-fit engagement in the recess of the pump housing.

The recess in the pump housing preferably has a substantially cuboid shape, and the attachment part has a substantially cuboid main body.

In a preferred embodiment, the connection element and the connector piece or attachment opening are arranged on two different sides of the attachment part, in particular on two sides lying at right angles to each other.

The pump-side attachment part is preferably designed in one piece.

In a preferred embodiment, the pump-side attachment part or pump-side end connector has a patient-side connection element for connection to a service tube, a pump-side connection element for connection to a service unit arranged in the pump housing, and a service channel that connects these two connection means and extends through the attachment part. The patient-side connection element for connection to the service tube and the connection element for connection to the patient-side drainage tube are preferably arranged on the same side of the attachment part. The connection between pump-side attachment part and pump housing is also preferably made without connection tubes or intermediate tubes.

Other advantageous embodiments will become evident from the dependent patent claims.

BRIEF DESCRIPTION OF THE DRAWINGS

The subject matter of the invention is explained below on the basis of a preferred illustrative embodiment depicted in the attached drawings, in which.

WAYS OF IMPLEMENTING THE INVENTION

Figure 1:
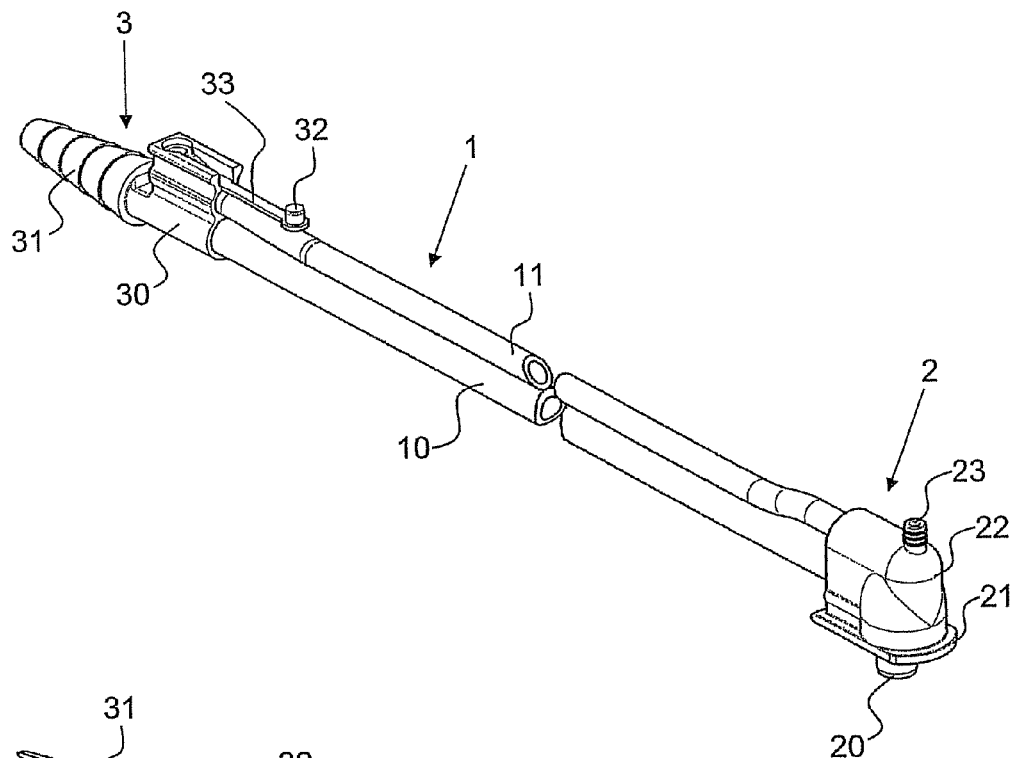
FIG. 1 shows a perspective view of a drainage tube unit according to the invention.

FIG. 1 shows a drainage tube unit as used in the drainage aspiration devices mentioned at the outset. It is composed mainly of a tube system 1 with two or more tubes 10, 11, a pump-side attachment part 2 and preferably, but not necessarily, a patient-side attachment part 3. According to the invention, however, an individual single-lumen drainage tube can also be used.

The tubes 10, 11 shown here are preferably single-lumen tubes independent of each other. They are preferably made of silicone or PVC. They extend separate from each other at their ends. Between the ends, they can be adhesively bonded to each other, welded to each other or otherwise connected. In the figures, the tubes are not shown at their full length and are instead interrupted.

The two tubes preferably have different diameters. The thicker tube 10 forms an underpressure and drainage line for aspirating the body fluid. The thinner tube 11 forms a service line which, for example, permits the above-described or similar pressure measurement and/or cleaning of the drainage line. Both applications can be carried out jointly but one after the other if the suction unit at the pump-side end of the service line has a valve which is closed for the underpressure measurement during the aspiration procedure. During the cleaning mode, however, the valve is opened. The service line can also be used in other known ways.

The two tubes 10, 11 preferably extend parallel to each other along approximately the entire length, and their ends in particular open out in parallel, but spaced apart from each other, into the respective attachment parts or elements 2, 3. Spaced apart means that they can bear on each other or that they can leave a space free between them. At least in one of the two parts, they protrude inwards on the same face of the attachment part. The ends are inserted into the attachment parts 2, 3, adhesively bonded in them or otherwise secured.

The pump-side attachment 2 will first be described below. Pump-side in this context, however, simply means remote from the patient. Instead of being in a pump housing, the attachment part can instead also be arranged in a fluid collection container or other unit remote from the patient. Therefore, where the term pump-side is used below, this also means the container side.

The pump-side attachment part 2 is preferably made of plastic by injection moulding, and it is preferably designed in one piece.

Figure 4:
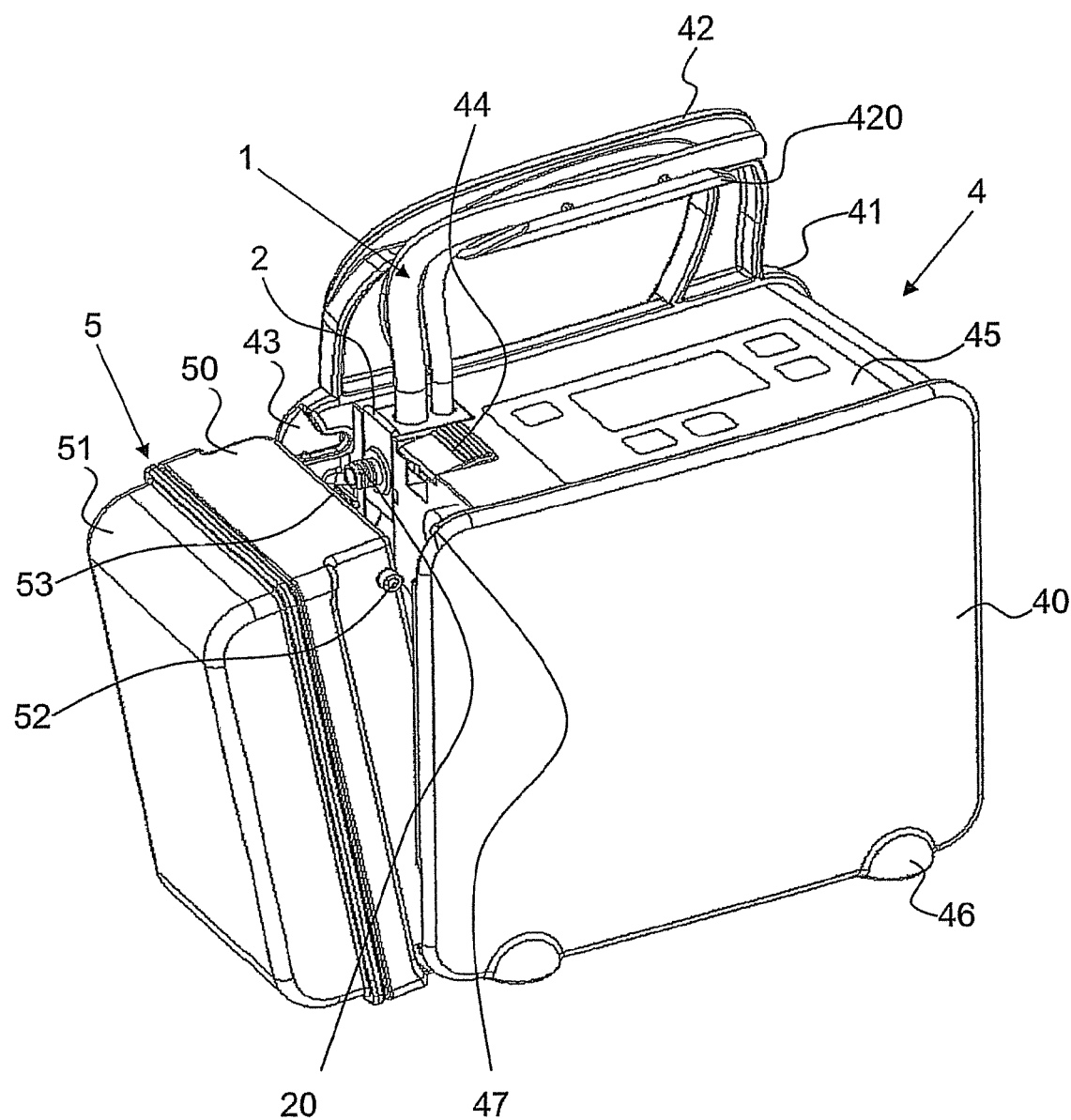
FIG. 4 shows a perspective view of a drainage pump device with a variation of a pump-side attachment part of the drainage tube unit according to the invention.

It has a substantially cuboid main body 2, which is here provided with a peripheral flange 21. With this flange 21, the part 2 can be introduced with a form fit into a corresponding recess of the pump housing and held therein, as is shown in FIG. 4.

Figure 2:
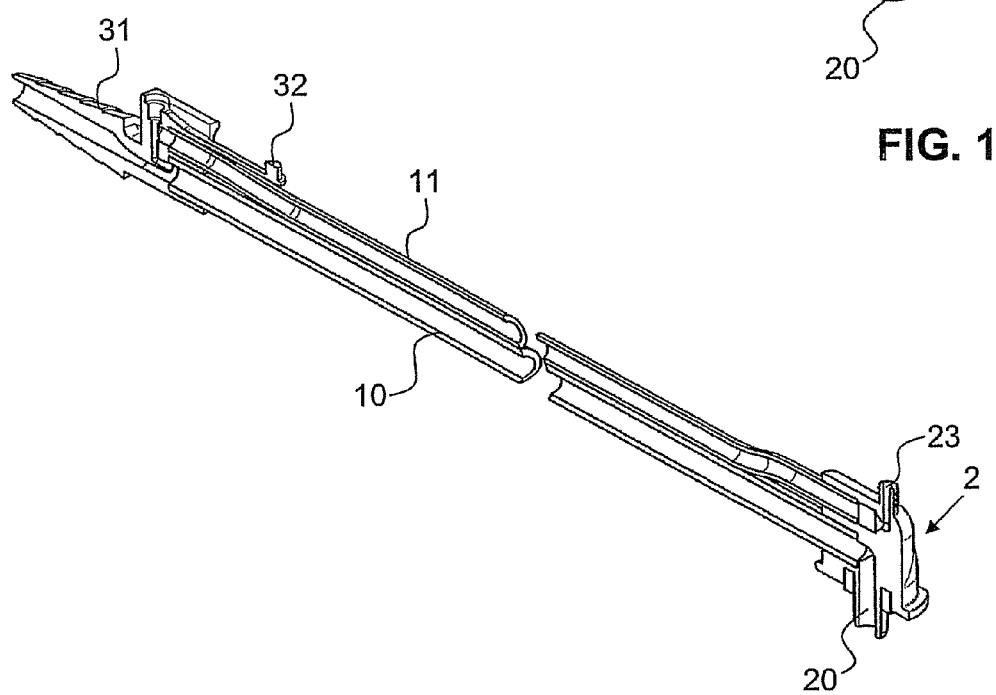
FIG. 2 shows a perspective view through a drainage tube unit according to FIG. 1 when sectioned in the longitudinal direction.
Figure 3:
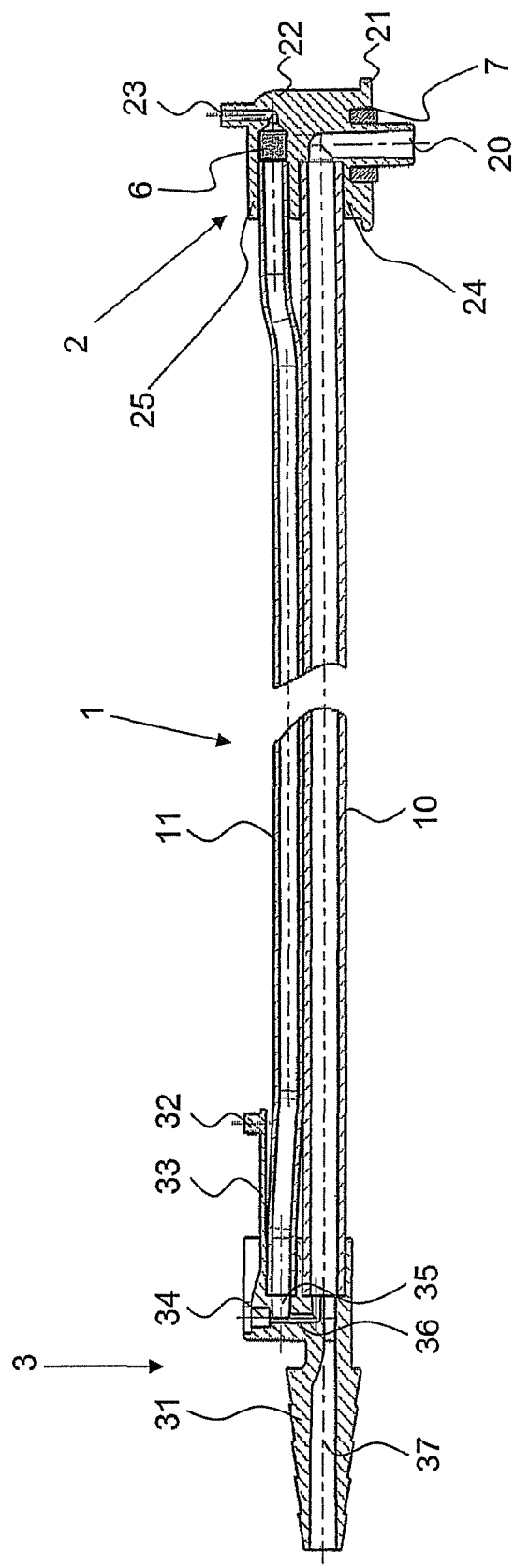
FIG. 3 shows a longitudinal section through the drainage tube unit according to FIG. 1.

As can be seen from FIGS. 2 and 3, the attachment part 2 has two channels 24, 25, and the pump-side ends of the drainage and service tubes 10, 11 are inserted into the mouth openings that lie parallel to each other but spaced apart from each other.

A filter 6 is preferably arranged in the pump-side service channel 25. This, for example, is a hydrophobic filter and/or a bacterial filter. The service channel 25 then narrows and bends off at right angles with respect to the mouth. It ends in a service inlet 23 that protrudes in the form of a connector piece from the main body 22. This service inlet 23 serves for connection to a service unit of the suction device.

The pump-side drainage channel 24 also bends off at right angles with respect to its mouth and likewise ends in a connector piece, the pump-side drainage outlet 20, protruding from the main body 22. This outlet 20 serves for connection to a fluid collection container. The outlet 20 is here arranged at right angles to the mouth of the tube 10, but it can also be arranged on a different face of the main body 22 than the mouth face. The same applies for the service inlet 23 in relation to the mouth of the service tube 10.

The aspirated fluid passes through the drainage outlet 20 into the container. To ensure leaktightness, a peripheral groove can be provided round the drainage outlet 20 in the main body 22. The groove can be provided with a sealing ring. The drainage outlet 20 is preferably arranged on a face of the main body 22 that lies opposite the face with the service inlet 23.

Instead of the pump-side attachment part 2 or end connector described here, a more simply configured part can also be used that is held on or in the pump housing 4. For example, the service channel and the service attachments can be dispensed with if only an individual drainage tube and no service tubes are to be attached.

On the patient side, it is possible, but not necessary, for a patient-side attachment part 3 to be present. If it is present, it is preferably also made of plastic by injection moulding. It too is preferably designed in one piece. A variant with a service tube is described below. It goes without saying that the part has a simpler design, particularly without connection channel and service channel, if no service channel is to be connected, but instead only an individual drainage tube.

The patient-side attachment part 3 has a main body 30 with two mouths for the patient-side ends of the drainage tube 10 and of the service tube 11, which mouths are parallel to each other but spaced apart from each other. A patient-side drainage inlet 31, formed integrally on this main body 30, has a conical shape and is provided with steps and narrows towards its free end. It has a Christmas tree shape in cross section. The drainage inlet 31 preferably extends approximately in axial alignment with the mouth of the patient-side end of the drainage tube 10, such that the patient-side drainage channel 37 in the interior of the attachment part extends approximately in a straight line.

The patient-side end of the service tube 11 opens into a mouth of a patient-side service channel 35, which preferably has a smaller diameter than the drainage channel 37. The channel 37, also like all the other channels described, has a step that serves as an abutment for the tube 11. The mouths described above are understood as extending as far as these steps.

The service channel 23 ends in the main body 30 and there opens into a connection channel 36, which is preferably perpendicular to the service channel 23. The connection channel 36 has the same diameter as or preferably a smaller diameter than the service channel 35. It terminates at one end in a right-angled bend in the drainage channel 37, preferably at the step to the mouth. Its other end forms an opening 34 to the outside, which opening 34 is preferably arranged perpendicular to the mouths in the main body 30.

This opening 34 is closed by a sealing closure 32, in this case a stopper. In the figure, it is shown still in the open state, it is preferably already closed in this configuration, In fact it is preferably already closed on ejection from the injection moulding machine, that is to say long before the tubes 10, 11 are secured.

The sealing closure 32 is preferably produced in one piece with the rest of the attachment part 3 and, as is shown, is therefore connected to the main body 30 via a band 33. This opening permits the one-piece production of this attachment part.

FIG. 4 shows a drainage pump device with which the drainage tube unit is preferably used. It serves to aspirate body liquids or fluids in the medical field, for example during or after surgical interventions, but also for wound drainage, thorax drainage, or for liposuction.

However, the tube unit can also be used in other drainage pump devices. It is preferable, but not essential, that the fluid collection container and, in the case of service tubes, also the pump unit can be connected to each other by means of the pump-side attachment part 2 without further intermediate lines.

Figure 7:
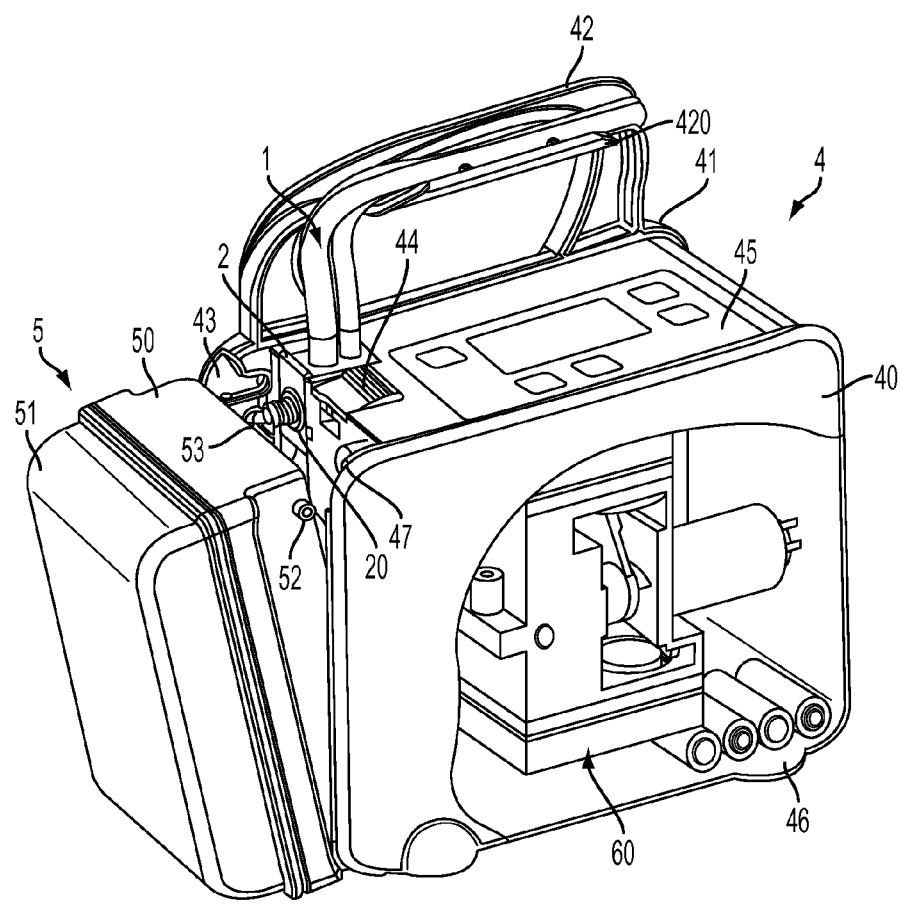
FIG. 7 shows a perspective view of the drainage pump device shown in FIG. 4, looking into the interior of the housing.

The drainage pump device shown here has a pump housing 4 which accommodates a vacuum pump or suction pump 60, as shown in FIG. 7, and electronics for operating the pump and for evaluating measured values obtained by way of the service tube.

The pump housing 4 preferably has a cuboid shape with a front wall 40, a rear wall 41, a handle 42 and feet 46. On an upper face of the housing 4, there is an operating panel 45 for operating the pump, preferably with a display.

The front wall 40 and the rear wall 41 jut out at one side and form a recess for a fluid collection container 5. This fluid collection container 5 is preferably composed of two container halves 50, 51 and is made of a transparent plastic.

The container 5 can be secured releasably on the pump housing 4, preferably being swiveled in and engaged in this position. For this purpose, the front wall 40 and the rear wall 41 of the pump housing 4 have upper and lower slide guides in which upper and lower securing pins 52 of the container 5 engage. Only one upper pin can be seen in the figure. The lower pins are already engaged, as can be seen from the oblique position of the container 5.

The container 5 has a hook 53 which is directed towards the housing 4 and in which a flip switch 44 of the housing 4 engages with a corresponding projection. In this way, the container 5 is fixed releasably on the housing 4.

Figure 5:
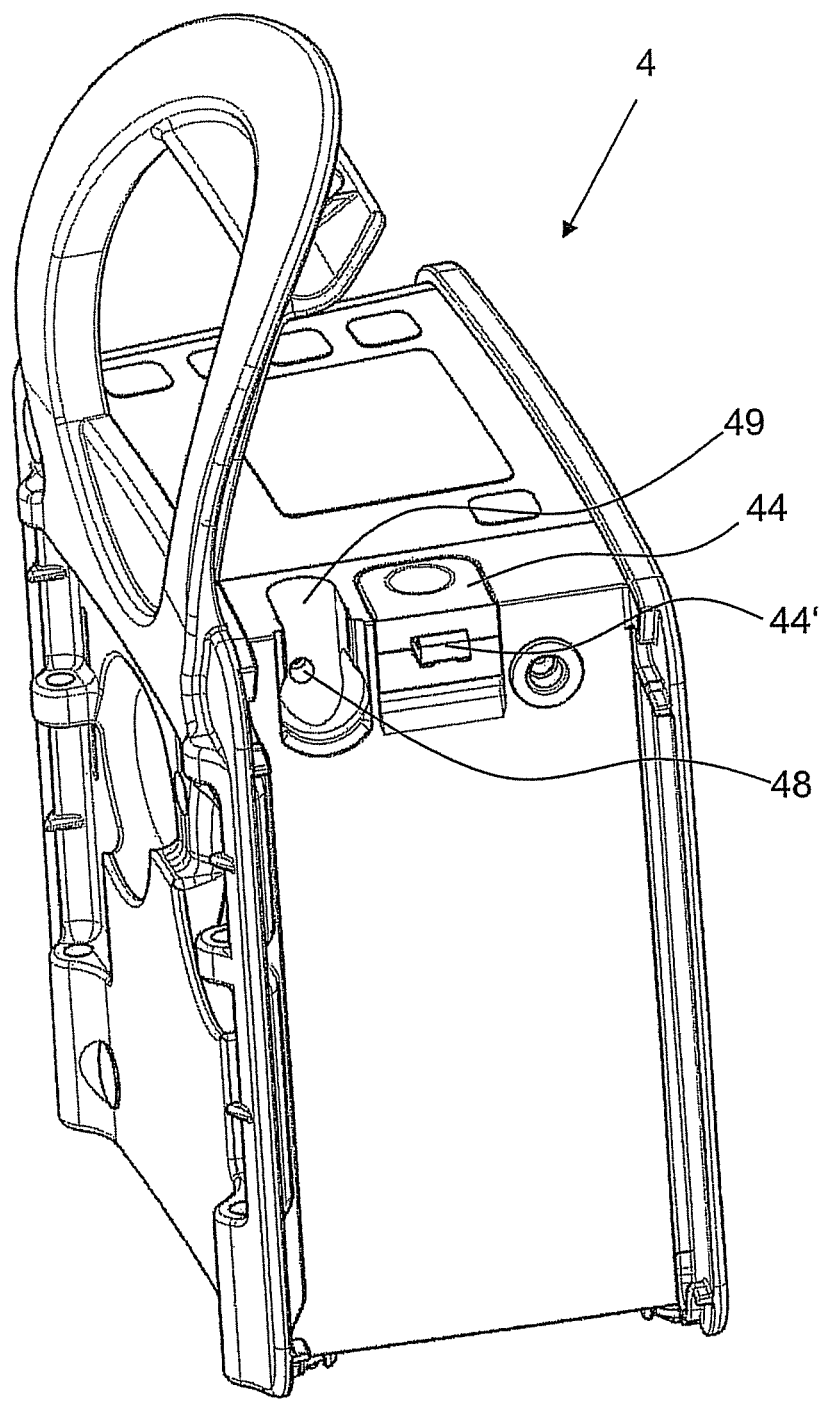
FIG. 5 shows a perspective view of a variation of the pump housing with its seat for the pump-side attachment part.
Figure 6:
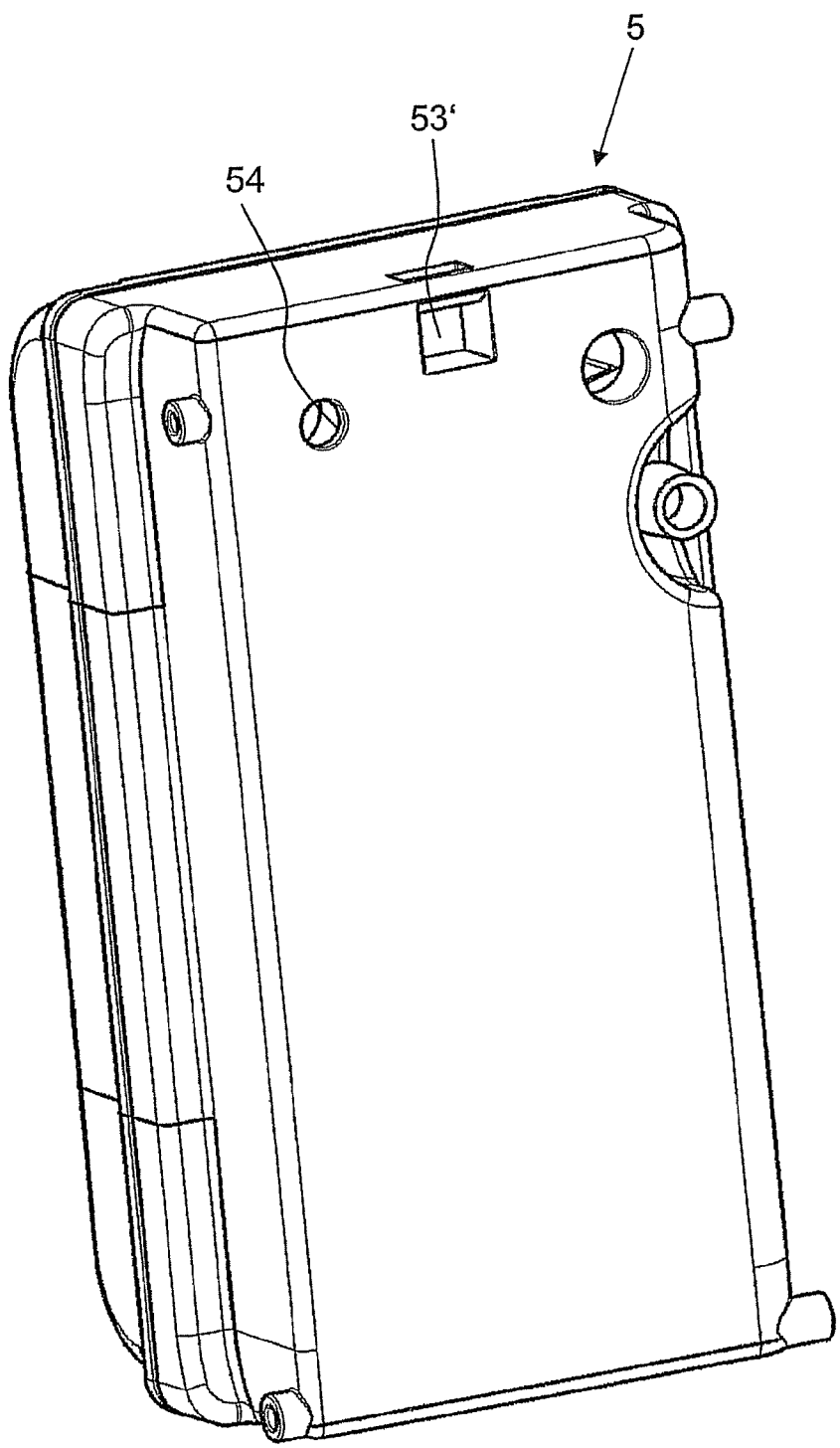
FIG. 6 shows a perspective view of the fluid collection container with its attachment opening for pluggable connection to the attachment part.

In the variant according to FIG. 5 the flip switch 44 comprises a hook 44' which engages with a recess 53' of the fluid collection container 5 shown in FIG. 6.

Facing the container 5, a suction connector 47 is provided on the housing 4. It has the shape of a nozzle, which engages in a corresponding opening of the container 5. In this way, an underpressure can be generated in the container 5 by means of the suction pump.

The housing 4 also has a substantially cuboid recess 49 into which the pump-side attachment part 2 of the drainage tube unit can be inserted and is held releasably therein with a form fit. In the variant according to FIG. 4, the recess 48 comprises plane side walls, so that the pump-side attachment part should comprise, contrary to the attachment part shown in FIGS. 1 to 3, plane side walls as well.

In the variant according to FIG. 5 the recess 49 comprises two plane and parallel to each other extending side walls and a curved, concave side wall connecting these two. This recess 49 matches the embodiment according to FIGS. 1 to 3.

The container-side drainage outlet 20 of the attachment part 2 of both variants is oriented towards the container 5. Through it the aspirated fluid passes into the container 5. As can be seen clearly in FIG. 6, the fluid collection container 5 has a corresponding attachment opening 54. Alternatively, the attachment part 2 can also be provided with an opening and the fluid collection container can be provided with a connector piece that matches said opening. In any case, a sealed connection is established, with a sealing means preferably being provided on at least one side, i.e. on the side of the attachment part or on the side of the fluid collection container. The sealing means is preferably a sealing ring made of an elastomer material. Here, it is an elastomer sealing ring 7 as shown in FIG. 3. However, other known ways of making a plug-type connection air-tight and liquid-tight are possible.

At right angles thereto, the tube system 1 with the two tubes 10, 11 opens into the pump-side attachment part 2. The tube system 1 in this example is routed along the housing 4 in a channel 420 arranged on the handle 42.

It will be seen from FIG. 5 that the pump housing 4 has a service opening 48 for receiving the service inlet 23 of the pump-side attachment part 2. The service inlet 23 of the attachment part 2 protrudes into the pump housing 4 and is connected to a corresponding control and/or evaluation unit. Depending on the particular application, an air-tight or liquid-tight connection is also present here. Here too, connector piece and opening can be provided the other way round.

Variants of the abovementioned example are conceivable. For example, the pump-side attachment part can be inserted in the housing or held on the latter at another place. The attachments can, for example, be at another angle to one another. The pump-side attachment part can be designed, for example, with a conical, cylindrical or other suitable shape.

The drainage pump unit according to the invention allows the fluid collection container to be replaced or emptied without removing the drainage tube and, therefore, without disturbing the patient.

LIST OF REFERENCE NUMBERS 1 tube system
10 drainage tube
11 service tube
2 pump-side attachment part
20 pump-side drainage outlet
21 flange
22 main body
23 pump-side service inlet
24 pump-side drainage channel
25 pump-side service channel
3 patient-side attachment part
30 main body
31 patient-side drainage inlet
32 sealing cover
33 band
34 opening
35 patient-side service channel
36 connection channel
37 patient-side drainage channel
4 pump housing
40 front wall
41 rear wall
42 handle
420 channel
43 slide guide
44 flip switch
44' hook
45 operating panel
46 foot
47 suction connector
48 service inlet
49 recess
5 fluid collection container
50 first half of container
51 second half of container
52 securing pin
53 hook
53' recess
54 attachment opening
6 filter
7 sealing ring
60 suction pump assembly

The invention claimed is:

1. A drainage pump unit for aspirating body fluids by means of a suction pump, the drainage pump unit comprising a drainage pump device with a pump housing for receiving the suction pump, and a fluid collection container that can be secured releasably on the pump housing, wherein the drainage pump unit also comprises a pump-side attachment part which has a connection element for connection to a patient-side drainage tube, wherein the attachment part is held releasably on the pump housing, and wherein the attachment part has a connector piece onto which an attachment opening of the fluid collection container can be fitted, or wherein the attachment part has an attachment opening into which a connector piece of the fluid collection container can be inserted, the connection element and the connector piece of the attachment part or the attachment opening of the attachment part being connected to each other via a drainage channel extending through the attachment part, wherein the fluid collection container can be removed from the pump housing without the attachment part, including the connection element and the connector piece, or the attachment opening having to be removed from the pump housing.

2. The drainage pump unit according to claim 1, in which the pump housing has a recess in which the attachment part is held releasably.

3. The drainage pump unit according to claim 2, in which the recess is located in a wall of the pump housing directed towards the fluid collection container.

4. The drainage pump unit according to claim 3, in which the recess extends as far as an edge of the wall and thus forms a corner piece.

5. The drainage pump unit according to claim 1, in which the attachment part is hold in a form-fit engagement in the recess of the pump housing.

6. The drainage pump unit according to claim 1, in which the recess in the pump housing has a substantially cuboid shape, and the attachment part has a substantially cuboid main body.

7. The drainage pump unit according to claim 1, in which the connection element and the connector piece of the attachment part or the attachment opening of the attachment part are arranged on two different sides of the attachment part.

8. The drainage pump unit according to claim 1, in which the attachment part is designed in one piece.

9. The drainage pump unit according to claim 1, in which the attachment part has a patient-side connection element for connection to a service tube, a pump-side connection element for connection to a service unit arranged in the pump housing, and a service channel that connects these two connection means and extends through the attachment part.

10. The drainage pump unit according to claim 9, in which the patient-side connection element for connection to the service tube and the connection element for connection to the patient-side drainage tube are arranged on the same side of the attachment part.

11. The drainage pump unit according to claim 2, wherein the attachment part is plugged into the recess.

12. The drainage pump unit according to claim 4, wherein the edge is an upper edge.

13. The drainage pump unit according to claim 7, wherein the connection element and the connector piece of the attachment part or the attachment opening of the attachment part are arranged on two sides lying at right angles to each other.

* * * * *